(12) United States Patent
Buonomo et al.

(10) Patent No.: US 6,242,660 B1
(45) Date of Patent: Jun. 5, 2001

(54) CATALYTIC SYSTEM AND PROCESS FOR DEHYDROGENATING ETHYLBENZENE TO STYRENE

(75) Inventors: Franco Buonomo, S. Donato Milanese; Domenico Sanfilippo, Paullo; Rodolfo Iezzi, S. Donato Milanese; Emilio Micheli, Milan, all of (IT)

(73) Assignee: Snamprogetti S.p.A., S. Donato Milanese (IT)

( * ) Notice: Subject to any disclaimer, the term of this patent is extended or adjusted under 35 U.S.C. 154(b) by 0 days.

(21) Appl. No.: 09/373,188

(22) Filed: Aug. 12, 1999

Related U.S. Application Data

(62) Division of application No. 09/100,243, filed on Jun. 19, 1998, now Pat. No. 5,994,258.

(30) Foreign Application Priority Data

Jun. 20, 1997 (IT) .......................................... MI97A001463

(51) Int. Cl.[7] .................................................. C07C 5/32
(52) U.S. Cl. ........................................ 585/445; 502/243
(58) Field of Search ................................ 585/445, 444; 502/243

(56) References Cited

U.S. PATENT DOCUMENTS

| | | |
|---|---|---|
| 4,038,215 | 7/1977 | Manning . |
| 4,711,930 | 12/1987 | Hoelderich et al. . |
| 4,746,643 | 5/1988 | Buonomo et al. . |
| 5,001,291 | 3/1991 | Holt et al. . |
| 5,143,886 | 9/1992 | Iezzi et al. . |
| 5,308,822 | 5/1994 | Iezzi et al. . |
| 5,414,182 | 5/1995 | Iezzi et al. . |
| 5,633,421 | 5/1997 | Iezzi et al. . |

FOREIGN PATENT DOCUMENTS

| | | |
|---|---|---|
| 0206193 | 12/1986 | (EP) . |
| 0336622 | 10/1989 | (EP) . |

*Primary Examiner*—Bekir L. Yildirim
(74) *Attorney, Agent, or Firm*—Oblon, Spivak, McClelland, Maier & Neustadt, P.C.

(57) ABSTRACT

Catalytic system for dehydrogenating ethylbenzene to styrene, containing chromium oxide, tin oxide, at least one oxide of an alkaline metal (M) and an alumina carrier, in delta or theta phase or in a mixture of delta+theta or theta+alpha or delta+theta+alpha phases, modified with silica, and characterized in that:

- the chromium, expressed as $Cr_2O_3$, is in a quantity of between 6 and 30% by weight;
- the tin, expressed as SnO, is in a quantity of between 0.1 and 3.5% by weight;
- the alkaline metal, expressed as $M_2O$, is in a quantity of between 0.4 and 3% by weight;
- the silica is in a quantity of between 0.08 and 3% by weight, the complement to 100 being alumina.

13 Claims, 3 Drawing Sheets

CATALYTIC SYSTEM AND PROCESS FOR DEHYDROGENATING ETHYLBENZENE TO STYRENE

This is a div. of Ser. No. 09/100,243, filed Jun. 19, 1998, U.S. Pat. No. 5,994,258.

The present invention relates to a catalytic system and the process using this system for dehydrogenating ethylbenzene to styrene.

Styrene is an important intermediate for the production of plastic materials and rubber.

It is mainly used in the production of polystyrenes (GPPS crystals, shock-resistant HIPS and expandable EPS), acrylonitrile-styrene-butadiene (ABS) and styrene-acrylonitrile (SAN) copolymers of styrene-butadiene rubbers (SBR).

At present styrene is mainly produced by means of two processes:
  by the dehydrogenation of ethylbenzene (EB) (which covers about 90% of the world capacity (App. Cat. 133, 1995, 219));
  as a coproduct in the epoxidation of propylene with ethylbenzene hydroperoxide with catalysts based on molibden complexes.

Two alternative ways of producing the monomer have recently been studied and in some cases developed on an industrial scale:
  the oxidative dehydrogenation of ethylbenzene;
  the dehydrogenation of ethylbenzene followed by the oxidation of hydrogen.

We shall now only consider the production of styrene by the dehydrogenation of ethylbenzene as this is the method followed by the process of the present invention.

The dehydrogenation reaction of ethylbenzene to styrene has various particular characteristics which should be taken into consideration for the technological design.

The first is that the reaction is controlled by the thermodynamic equilibrium and therefore the conversion per passage cannot be total.

The degree of dehydrogenation increases with the rise in temperature and reduction of the total pressure, the reaction taking place, at a constant pressure, with an increase in volume.

To obtain economically acceptable conversions, the thermodynamics makes it compulsory for the reaction to be carried out within the range of 540–630° C. It is also necessary to operate in the presence of a suitable catalyst owing to the low rate at which the ethylbenzene dehydrogenates, also at these thermal levels.

Owing to the rather high operating temperatures, parasite reactions inevitably take place, these generally being characterized by a greater activation energy with respect to the dehydrogenation energy. The main product is therefore accompanied by by-products, mainly consisting of toluene, benzene, coke and light products. The function of the catalyst is to direct the reaction towards the desired product.

The last important aspect consists in the fact that the reaction is strongly endothermic, with a reaction heat equal to 28 Kcal/mole of styrene, corresponding to 270 Kcal/kg of styrene produced. The high heat required and high thermal levels at which it must be exchanged are the aspects which mainly influence the technological design. The technologies at present sold (Fina/Badger and Lummus/UOP Classic SM processes) satisfy the demands imposed by the thermodynamics by adopting a technological system which comprises:
  the use of several adiabatic reactors in series, with intermediate heating steps, in which the temperature is between 540 and 630° C. with contact times more or less of tenths of a second;
  The use of radial flow reactors operating under vacuum in which the pressure is between 0.3 and 0.5 atm;
  the use of water vapor in co-feed with the charge to be dehydrogenated.

Water is the main component being fed to the reactor. The typical molar concentration is 90%. Often however a concentration of more than 90% is adopted to lengthen the chemical life of the catalyst.

The vapor has several functions:
  it reduces the partial pressure of the products and therefore favourably shifts the thermodynamic equilibrium;
  by the reaction of water gas, it contributes to decoking the catalyst, as there is no burn-off of the catalyst with air;
  it supplies all the heat necessary for the dehydrogenation of EB.

With present technologies, conversions of 60–65% are reached with selectivities to styrene of more than 90% by weight with an optimized catalyst mainly based on iron oxide promoted with alkalies.

In spite of the performances, the present technologies have disadvantages Which are mainly due to the following aspects:
  use of huge quantities of superheated vapor ($H_2O$/EB= 9.0–9.8 (molar) with a temperature of over 700° C.: this necessitates the use of super-heating ovens and therefore high investment costs;
  aging of the catalyst: this makes it necessary to replace it after about 18–36 months of operation; to do this it is necessary to stop the unit and interrupt production for the period required for its substitution; it is possible to prolong the life by increasing the ratio $H_2O$/EB, but this further compromises the energy balance;
  recuperation of energy not as yet optimized: the present technologies, in fact, only recuperate the sensitive heat of the vapor and not also the latent heat;
  carrying out the reaction under vacuum (average absolute pressure of 0.4 atm) and therefore in an extremely dilute phase in EB: the partial pressure of the EB is on an average equal to 0.04 atm.

We have surprisingly found that by using a particular catalytic system mainly consisting of $Cr_2O_3$ supported on an alumina modified with silica, to which tin oxide has been added, the dehydrogenation technology of ethylbenzene is significantly improved.

The catalytic system of the present invention, for dehydrogenating ethylbenzene to styrene, contains chromium oxide, tin oxide, at least one oxide of an alkaline metal ($M_2O$) and an alumina carrier, in delta or theta phase or in a mixture of delta+theta or theta+alpha or delta+theta+alpha phases, modified with silica, and is characterized in that:
  the chromium expressed as $Cr_2O_3$, is in a quantity of between 6 and 30% by weight, preferably between 13 and 25%;
  the tin, expressed as SnO, is in a quantity of between 0.1 and 3.5% by weight, preferably between 0.2 and 2.8%;
  the alkaline metal, expressed as $M_2O$, is in a quantity of between 0.4 and 3% by weight, preferably between 0.5 and 2.5%;
  the silica is in a quantity of between 0.08 and 3% by weight,
  the complement to 100 being alumina.

Figure 1:
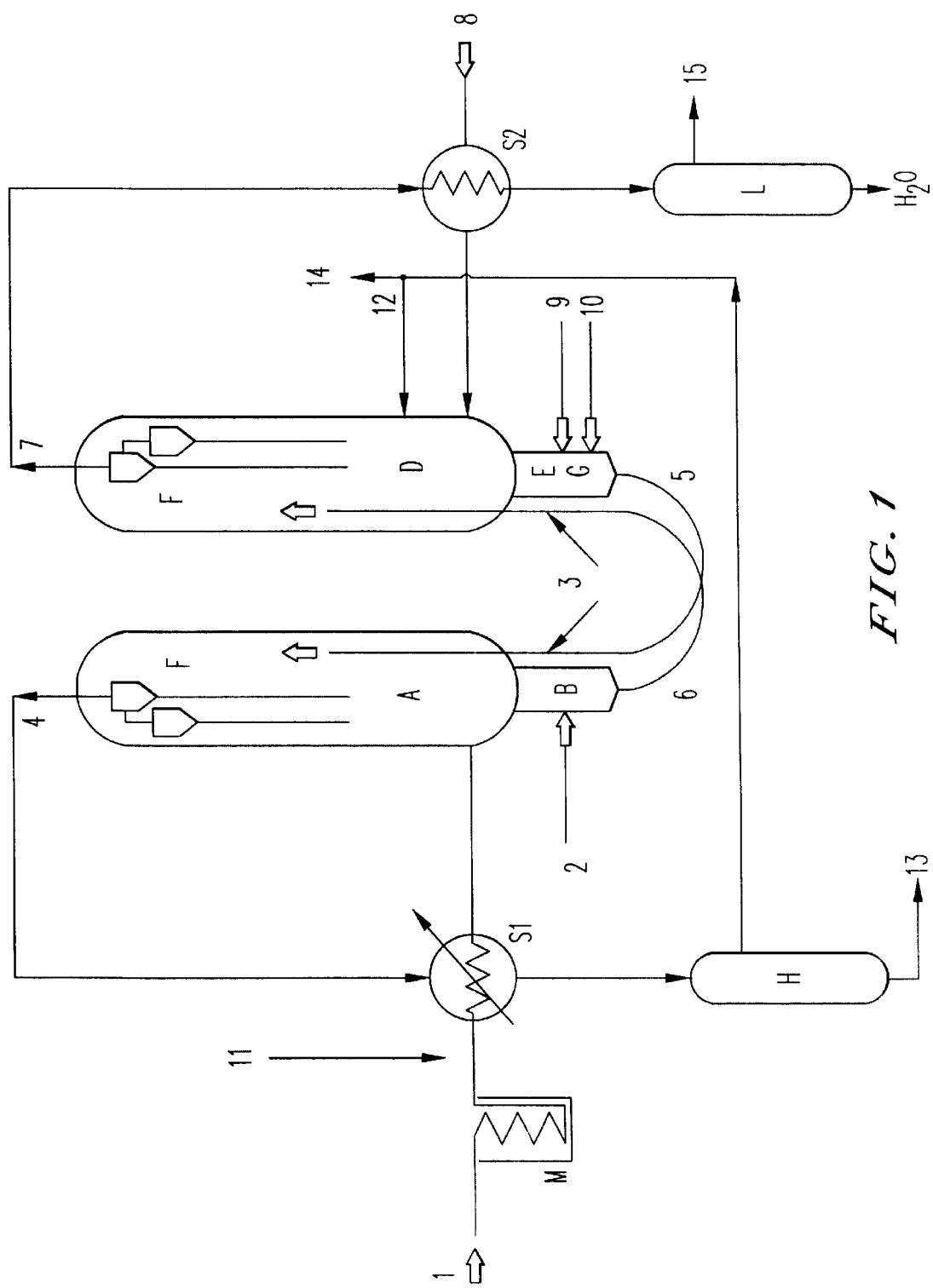
FIG. 1, shows an embodiment of the reactor-regenerator apparatus of the invention.

DETAILED DESCRIPTION OF THE PREFERRED EMBODIMENT:

The alkaline metal, preferably potassium, is used for moderating the acidity of the supporting alumina.

With respect to the surface area of the carrier, this is preferably less than 150 m$^2$/g, determined with the BET method.

The process for preparing the catalytic system described above, essentially consists in dispersing a compound of chromium, an alkaline metal and tin on a carrier consisting of alumina (in delta or theta phase or in a mixture of delta+theta or theta+alpha or delta+theta+alpha chases) and silica.

Some of the procedures for dispersing the chromium oxide, potassium oxide and tin oxide (stannous and/or stannic) onto the carrier are listed below, it being understood that the invention is not limited to these.

This dispersion treatment can consist in the impregnation of the carrier with a solution containing the precursors of chromium, potassium and tin oxides, followed by drying and calcination, or by an ionic absorption, followed by the separation of the liquid and drying and calcination of the solid. Among those listed above the preferred procedure is impregnation, according to the "incipient wetness" method of the carrier with the solution containing all the precursors of the active prinicples.

With respect to the tin, other procedures are listed with which it can be added to the catalytic system:
- addition of the tin to the carrier before the dispersion of the precursors of chromium and potassium oxide;
- treatment of the solid containing chromium and potassium oxide by ionic exchange, impregnation, etc., with a solution containing a compound of tin;
- deposition of the tin via "vapor deposition" onto the carrier, before adding the precursors of chromium oxide and potassium oxide, using a volatile compound of the species to be deposited;
- deposition of the tin via "vapor deposition" onto the solid containing alumina, chromium oxide and potassium oxide, using a volatile compound of the species to be deposited.

Among the above procedures, coimpregnation of the carrier with the solution containing the precursors of the active principles (chromium oxide, potassium oxide and tin oxide) and deposition via "vapor deposition" of the tin, are preferred.

Precursors of stannous and/or stannic oxide which can be used are both inorganic and organic salts of tin, or organometallic derivatives.

The inorganic or organic salts, not very soluble in water, can be used after controlling the pH of the solution which influences their solubility.

The organometallic derivatives are used by adopting organic solvents in which they are dissolved to be added to the catalytic system according to the procedure described above.

The catalytic system claimed can be applied to any dehyrogenation technology of ethylbenzene using a fixed, fluid or mobile bed.

The process for dehydrogenating ethylbenzine to styrene, which is a further object of the present invention, consists in:

a) reacting in a reactor, operating at a temperature of between 450 and 700° C., at a pressure of between 0.1 and 3 atm and with a GHSV space velocity of between 100 and 10000 h$^{-1}$ (normal liters of hydrocarbon/h× liter of catalyst), the ethylbenzene with the catalytic system described above, preferably diluted with an inert product at a weight concentration of the catalytic system of between 5 and 50%.

b) regenerating the catalytic system in a regenerator by burning the coke deposited during the reaction phase operating at a temperature of over 400° C.

A catalytically inert material can be used as inert product, such as for example, alpha-alumina, possibly modified with alkaline metal oxides, and/or silica, etc.

The process is preferably carried out in a fluid bed system essentially consisting of a reactor in which the dehydrogenation reaction takes place and a regenerator in which the catalyst is regenerated by burning the coke deposited during the reaction phase.

In the reactor-regenerator system, the catalyst in the fluid state continuously circulates between the reactor and regenerator, allowing the process to operate in continuous and the heat necessary for the reaction is removed from the regenerated catalyst, which reaches the reactor at a temperature which is higher than the average reaction temperature.

The catalyst is maintained in the fluid state in the reactor by the reagent gas (ethylbenzene) which enters the catalytic bed from below, by means of a specific distribution system.

It is advisable to also feed an inert gas together with the ethylbenzene (nitrogen, methane, hydrogen, water, etc.) in a volumetric ratio inert gas/ethylbenzene preferably between 1 and 6, more preferably between 2 and 4.

The reacted gas leaves the reactor from above, after passing through a system of cyclones or another suitable separation system of the powders; it can subsequently be sent to a heat exchanger for the preheating of the feeding and then to the separation section where the styrene produced is recovered, whereas the non-reacted charge is recycled to the dehydrogenation and the uncondensable products are separated and can be used in the regenerator as fuel gas.

The catalyst, in the fluid state, moves in the reactor in countercurrent with respect to the gas phase: it enters the catalytic bed from above, by means of a distributor which divides it equally onto the surface of the bed, and leaves the reactor from below, passing by gravity into a desorption zone, again part of the reactor, with a diameter less than or equal to the reaction zone, where the displacement of the interparticle gas and desorption of the intraparticle gas take place, by introducing nitrogen or methane from below, so that the displaced or desorbed gas re-enters the reactor avoiding losses of reagents or products.

The catalyst, still in the fluid state, is then pneumatically sent to the regenerator.

In the fluid bed reactor it is preferable to operate:
- at a temperature maintained, by acting on the flow-rate of the regenerated catalyst, at between 450 and 650° C. depending on the reaction desired;
- at a pressure which is atmospheric or slightly higher;
- at a space velocity of between 100 and 1000 h$^{-1}$ (Nliters of ethylbenzene and inert gas per hour and per liter of catalyst), more preferably between 150 and 200;
- with a residence time of the catalyst varying in the fluid bed zone from 5 to 30 minutes, more preferably from 10 to 15 minutes, in the desorption zone from 0.2 to 10 minutes.

The pneumatic transport system from the reactor to the regenerator consists of a transport line with at least one zone in which the catalyst moves downwards, preferably maintained under intermediate conditions between the minimum fluidization and the minimum formation of bubbles, by the introduction of suitable quantities of gas at appropriate heights and a zone in which the catalyst moves upwards until it reaches the upper part of the catalytic bed of the regenerator, by the introduction of gas at the base which considerably reduces the density of the emulsion.

The regenerator preferably has dimensions which are similar to those of the reactor; these dimensions are due to the necessity of maintaining the catalyst in the regenerator for a time which is sufficient for its regeneration.

A suitable distributor disperses the catalyst coming from the reactor onto the surface of the catalytic bed. The regeneration takes place inside the bed by the combustion of the coke deposited on the catalyst and the heating of the catalyst by the combustion of methane or fuel gas or by-products of the main reaction with air or oxygen or another combustion-supporting gas, at a higher temperature than the average temperature of the reactor.

Before being sent to the reactor the regenerated catalyst is subjected to reducing treatment, at temperatures of between 650 and 680° C. and for a time of between 0.2 and 10 minutes, to reduce the hexavalent chromium, and is then desorbed of the combustion and reduction products.

The movement of the gas and solid takes place in countercurrent also in the regenerator: air is sent onto the bottom of the catalytic bed, whereas the fuel gas is introduced at suitable heights along the bed.

The gas leaving the regenerator, consisting of nitrogen and combustion products, can pass through cyclones, or another system, situated in the upper part of the apparatus, to separate the powders drawn in, and subsequently, after leaving the regenerator, it can be sent to a heat exchanger for the preheating of the combustion air.

Before being discharged into the atmosphere, these gases can pass through a filter system or other devices for reducing the powder content to a few tens of mg per m$^3$ of gas.

As the combustion catalytically takes place at a temperature of less than 700° C., the content of carbon monoxide and nitrogen oxides in the discharge gases is such that further purification treatment is not necessary.

It is preferable to operate in the regenerator at a pressure which is atmospheric or slightly higher, at a space velocity of between 100 and 1000 h$^{-1}$ and with a residence time of the solid varying from 5 to 60 minutes, more preferably from 20 to 40 minutes.

The regenerated catalyst is transported to the reactor in the same way that the exhausted catalyst is transported to the regenerator.

The reactor-regenerator system thus conceived enables the operating parameters and performances to be kept constant for the entire technical life of the plant.

Aliquots of catalyst are periodically discharged from the system and substituted with equal aliquots of fresh catalyst, without ever having to interrupt the running of the plant.

The advantages of the use of a fluid bed reactor-regenerator system can be synthesized as follows:

- the heat is directly transferred to the reaction by the regenerated catalyst: there are no superheating ovens for the thermal exchange and the strong remixing of the fluid bed prevents the formation of high temperature points which would lower the selectivity;
- the fluid bed process makes it possible to recycle hydrogen;
- all the other operations are carried out in continuous and it is not necessary to modify the operating parameters during the whole life of the plant;
- the plant can operate with wide flexibility in terms of present productive capacity with respect to the project capacity;
- the reaction and regeneration take place in physically separated zones and there cannot be any mixing of hydrocarbon streams with streams containing oxygen;
- the process is carried out at atmospheric or a slightly higher pressure: there is therefore no possibility of external infiltrations of air into the reaction zone;
- no particular treatment is necessary for reducing the emissions of gaseous pollutants;
- the molar concentration inert products/ethylbenzene in the feed is much lower than in commercial technologies.

FIG. 1 shows a possible application of the reactor-regenerator scheme described above.

The feeding (ethylbenzene(1)) vaporized in (M) and mixed with the inert gas (11) enters the reactor (A) through a suitable distributor (not shown in the figure), whereas the gases after the reaction leave the reactor from line (4) after passing through the cyclones F, through the heat exchanger (S$_1$), where the ethylbenzene-inert product is preheated, and through the separator (H).

The liquid phase (13) is sent to distillation, whereas the uncondensable products are partly (12) sent to the regenerator (as fuel) and partly (14) for separation.

The regenerated catalyst (5) arrives, by the entry of gas (3), at the top of the catalytic bed and leaves the reactor (A) passing into the desorber (B), where it enters into contact with the desorbing gas (2). The catalyst subsequently enters the transport line (6), in which it is sent to the regenerator (D), and precisely to the upper part of the catalytic bed.

In this case a single line of gas inlet along the transport line, is shown (6). The transport line in this application is characterized in that it has a U-shaped connection between the downward and upward part. The catalyst descends along the regenerator (D), enters the reducer (E), then the desorber (G) and finally the transport line (5) and is sent to the reactor. The regeneration air enters (8), the fuel gas (12), the reduction gas (9) and the desorbing gas (10), again through suitable distributors (not shown in the figure).

The gases, after passing through the cyclones F, leave via (7), and are used for preheating the air (8), by means of the exchanger (S$_2$), for regeneration and are finally sent to the separator (L) in which the water is separated from the combustion products (15).

Several examples are provided together with comparative examples 1, 4 and 5, which should not be considered as limiting the present invention.

EXAMPLE 1

Comparative

A microspheroidal pseudobohemite is prepared to which silica has been added (1.2% w), with a particle diameter of between 5÷300 microns, by spray-drying a hydrated alumina sol and Ludox silica.

A sample of the pseudobohemite is subjected to thermal treatment consisting in a first calcination at 450° C. for an hour, followed by another at 1030° C. for 4 hours in a stream of dry air.

Figure 2:
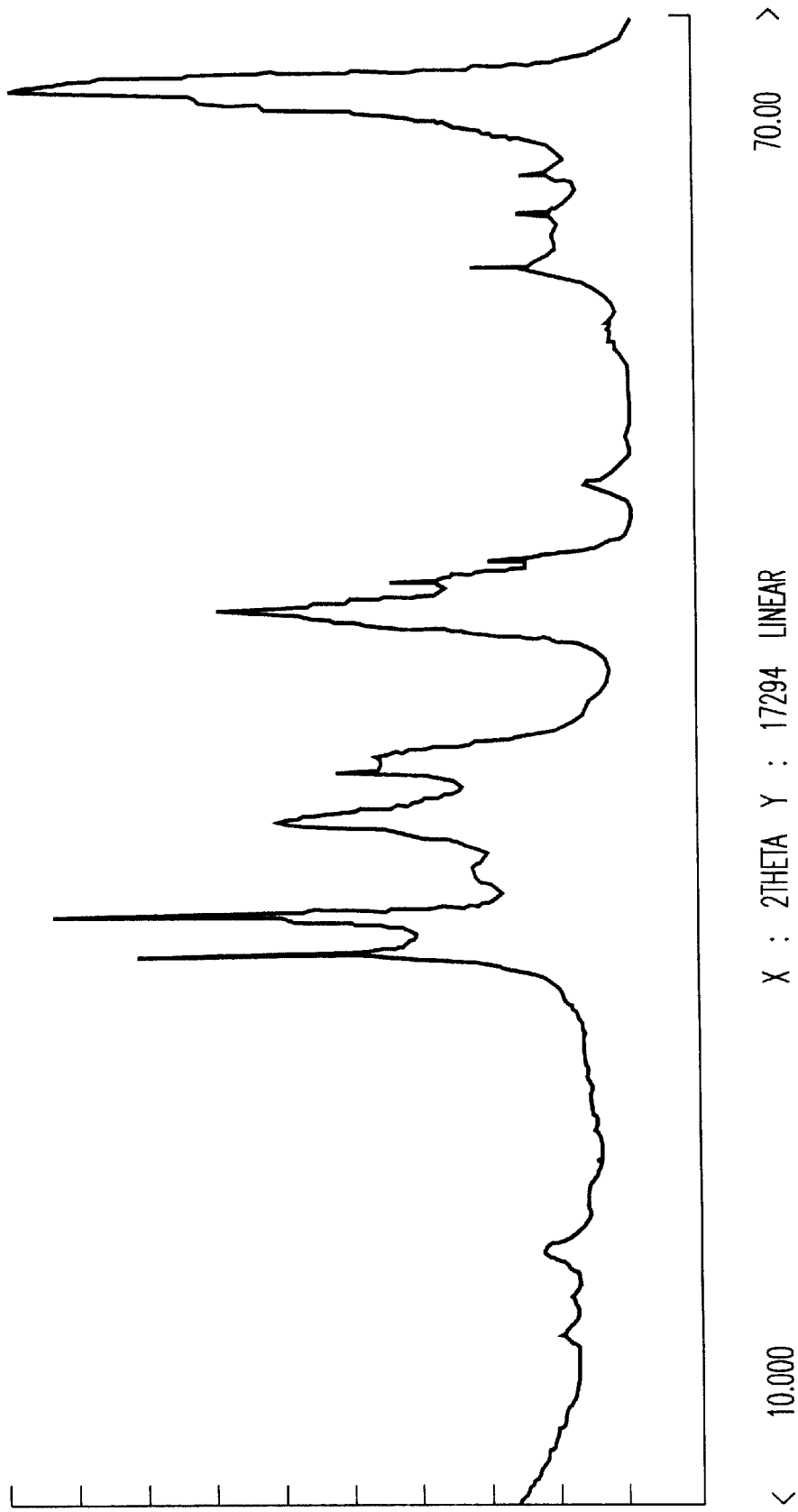
FIG. 2 shows an XRD spectrum of the calcined pseudobohemite of Example 1.

The product obtained has a specific surface of 100 m$^2$/g, a porosity of 0.34 cc/g and essentially consists of delta and theta transition aluminas, accompanied by a small quantity of alpha alumina (See the XRD spectrum in FIG. 2).

200 g of this alumina were impregnated, using the incipient wetness procedure, with 68 cc of an aqueous solution containing 67.5 gr of $CrO_3$ (99.8% w) and 6.4 g of OH (90% w) in deionized water, maintained at a temperature of 85° C. The impregnated product was left to rest for an hour at room temperature and subsequently dried at 90° C. for 15 hours. The dried product was finally activated, in a stream of dry air, at 750° C. for 4 hours.

The weight composition of the formulate proved to be as follows:
20% $Cr_2O_3$, 1.89% $K_2O$, 1.25% $SiO_2$, $Al_2O_3$ the complement to 100.

This formulate was tested in the dehydrogenation reaction of ethylbenzene to styrene, by mixing it with microspheroidal alpha-alumina (average diameter of the particles 50μ) in the weight proportions 1:3 (catalyst/alpha-alumina) within a temperature range of 550 to 600° C. The alpha-alumina was modified with potassium oxide 1% by weight as $K_2O$ by impregnation, using the "wetness impregnation" procedure, with an aqueous solution of potassium carbonate followed by drying and calcination at 750° C. for 4 hours.

The catalytic performances and the conditions under which they were obtained, are shown in table 1.

EXAMPLE 2

200 g of microspheroidal alumina, prepared as described in example 1, are impregnated according to the method described above with 68 cc of an aqueous solution containing: 68.8 g of $CrO_3$ (99.8% w), 6.52 g of OH (90% w) and 5.61 g of $SnC_2O_4$ (99.9% w) in deionized water, at the same temperature as example 1.

The impregnated product is treated as described in example 1 to give a catalyst having the following weight composition:
20% $Cr_2O_3$, 1.89% $K_2O$, 1.4% SnO, 1.22% $SiO_2$, $Al_2O_3$ the complement to 100.

The catalytic performances in the dehydrogenation reaction of ethylbenzene, obtained with the catalyst diluted in the same proportions as example 1, are shown in table 1.

EXAMPLE 3

A sample of the same catalyst prepared according to the procedure described in example 2 was diluted with the same alpha-alumina used in example 1 in the weight proportions 1:7 (cat/alpha-alumina) and tested in the dehydrogenation reaction of ethylbenzene.

The catalytic performances are indicated in table 1.

EXAMPLE 4

Comparative

Figure 3:
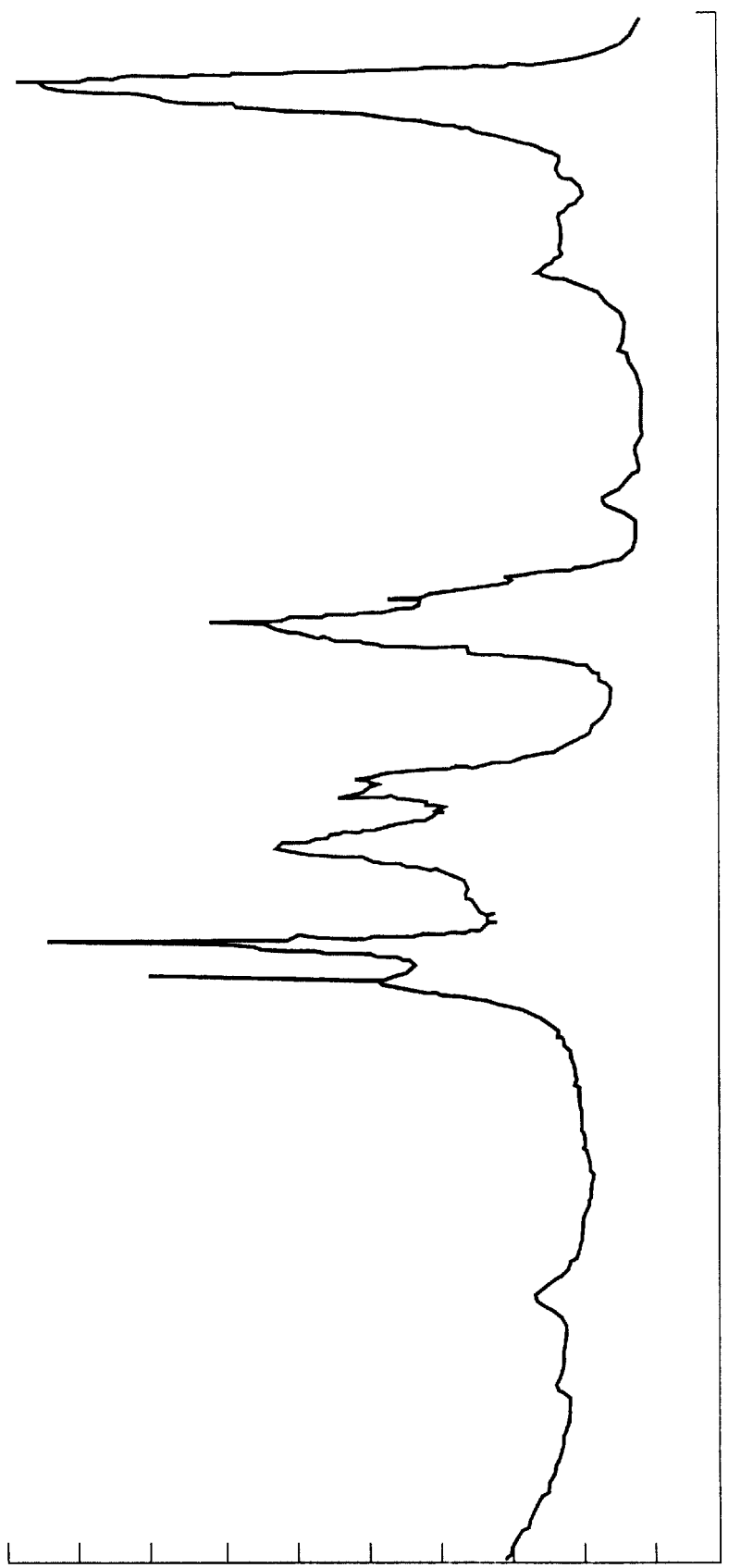
FIG. 3 shows an XRD spectrrum of the calcined psuedobohemite of Example 4

A 1000 g sample of the pseudobohemite prepared according to the procedure described in example 1, was subjected to thermal treatment consisting in a first calcination at 450° C. for an hour, followed by another at 1000° C. for 4 hours, in a stream of dry air. The calcined product has a surface area of 130 m²/g, a porosity of 0.49 cc/g and consists of delta and theta transition aluminas (See the XRD spectrum in FIG. 3).

150 g of this alumina were impregnated, using the incipient wetness procedure, with 74 cc of an aqueous solution containing 66.8 g of $CrO_3$ (99.8% w) and 5.36 g of potassium carbonate (45% w/w of OH) and maintained at the same temperature as example 1. The impregnated product was left to rest for an hour at room temperature and subsequently dried at 90° C. for 15 hours. The dried product was finally activated, in a stream of dry air, at 750° C. for 4 hours. The weight composition of the formulate proved to be as follows:
25% $Cr_2C_3$, 1% $K_2O$, 1.18% $SiO_2$, $Al_2O_3$ the complement to 100. This formulate was diluted with alpha-alumina in the weight proportions 1:7 (cat/alpha-alumina) and tested in the dehydrogenation reaction of ethylbenzene, obtaining the performances indicated in table 1.

EXAMPLE 5

Comparative

An aliquot of the same catalyst prepared according to the procedure described in example 4 was mixed with the same alpha-alumina used in example 1 in the same weight proportions 1:3 (cat/alpha-alumina) and the mixture was tested in the dehydrogenation reaction of ethylbenzene obtaining the catalytic performances indicated in table 1.

EXAMPLE 6

150 g of the same alumina used in example 4 were impregnated with 74 cc of an aqueous solution, at the same temperature as example 1, in which the following products were dissolved: 68.4 g of $CrO_3$ (99.8%), 5.49 g of potassium carbonate (45% solution w/w of OH) and 5.35 g of $SnC_2O_4$ (99.9% w/w). The drying and activation were carried out with the procedure described in example 1. The weight composition of the formulate proved to be as follows: 25% $Cr_2O_3$, 1% $K_2O$, 1.68% SnO, $Al_2O_3$ the complement to 100. The catalytic performances in the dehydrogenation of ethylbenzene, obtained with the formulate diluted with alpha-alumina in the weight proportions 1:7 (cat./alpha-alumina) are indicated in table 1.

EXAMPLE 7

A sample of catalyst prepared according to the procedure of example 6 and diluted with the same alpha-alumina and in the same proportions as example 1, was tested by feeding ethylbenzene diluted with a gaseous stream consisting of 8% by volume of $H_2$, 72% by volume of N, the complement ethylbenzene, to verify the effect of the hydrogen in the charge.

The performances are indicated in table 1.

EXAMPLE 8

The same catalyst used in example 7 was mixed with the alpha-alumina of example 1 in the same proportions and was tested by feeding ethylbenzene diluted with a stream consisting of 37% by volume of hydrogen, 43% by volume of $N_2$ and the complement ethylbenzene, to verify the catalytic performances of the formulate with a higher percentage of hydrogen in the charge.

The performances are indicated in table 1.

Catalytic Tests

The products prepared in examples 1–8 are tested in a fluid bed using a quartz reactor, capable of operating with a quantity of catalyst of between 50–100 cc, equipped with a distributor with a calibrated porosity also made of quartz, and a zone for the preheating of the ethylbenzene mixed with the inert product used.

An expander, also made of quartz, is placed on the head of the reactor, which has the function of decelerating the effluent allowing the fine particles to fall back into the catalytic bed. The expander is maintained at a temperature of 200° C., by placing it in an electrically heated oven, to avoid the condensation of the styrene, non-reacted ethylbenzene and non-condensable by-products which accompany the main reaction. The catalytic cycle, which is such as to simulate the behaviour on an industrial reactor, consists of a reaction phase, in which the ethylbenzene is fed with the inert product for a duration of 10 minutes, a stripping phase of 15 minutes, in which nitrogen is passed to liberate the catalyst from the products adsorbed, a regeneration phase, in which the regeneration gas consisting of air is fed for a duration of 45 minutes, a washing phase with nitrogen, with a duration of 10 minutes, a reduction phase in which the reducing gas consisting of methane is fed for the duration of 4 minutes to reduce the hexavalent chromium formed in the regeneration phase, a washing phase with nitrogen for a duration of 20 minutes followed by the reaction phase for a duration of 10 minutes.

The requisites of the industrial fluid bed dehydrogenation process are such that the regeneration must be carried out at temperatures which are higher than the reaction temperature: in the catalytic tests the regeneration and reduction were carried out at 660° C., whereas the reaction was carried out within the temperature range of 550–600° C.

The overall space velocity intended as normal-liters of ethylbenzene plus normal-liters of inert product (gas phase) was maintained at 600±5 Nl/h/lt of catalytic bed.

of the components was carried out with the internal standard procedure.

The gas recovered in the bag was analyzed by gas-chromatography using a gaschromatograph hp 5890 and using the external standard procedure for the dosage of the components. The contents of the bag were measured with a counter for the material balance. The coke deposited on the catalyst was burned with air and the effluent of the reactor collected in an evacuated bag of the same type as that used during the reaction phase.

The gas was analyzed via gas-chromatography to dose the concentration of the $CO_2$ and the volume measured to establish the quantity of coke generated in the reaction phase.

Once all the data had been obtained, they were registered in a personal computer to calculate the material balance, conversion and selectivity of the various products.

| | | | | | | | | | | | | Act. phase | | | | |
|---|---|---|---|---|---|---|---|---|---|---|---|---|---|---|---|---|
| Ex. | $Cr_2O_3$ % w/w | $K_2O$ % w/w | $SiO_2$ % w/w | SnO % w/w | Inert % v/v | $H_2$ feed % v/v | EB % v/v | Press. atm. | p EB | Temp °C. | LHSV** EB | in bed (% w/w) | EB Conv. % | Styrene sel. % mol. | Styrene cat.bed g/h/kg | Styrene act.phase g/h/kg |
| 1 comp. | 20 | 1.89 | 1.25 | abs. | 80* | abs. | 20 | 1.1 | 0.22 | 560 | 2.65 | 25 | 53 | 76 | 164 | 485 |
| 2 | 20 | 1.89 | 1.25 | 1.4 | 80* | abs. | 20 | 1.1 | 0.22 | 560 | 2.64 | 25 | 53 | 79 | 171 | 504 |
| 3 | 20 | 1.89 | 1.25 | 1.4 | 80* | abs. | 20 | 1.1 | 0.22 | 560 | 5.28 | 12.5 | 50 | 86 | 176 | 1035 |
| 4 comp. | 25 | 1.0 | 1.17 | abs. | 80* | abs. | 20 | 1.1 | 0.22 | 560 | 5.28 | 12.5 | 49 | 88 | 177 | 1038 |
| 5 comp. | 25 | 1.0 | 1.17 | abs. | 80* | abs. | 20 | 1.1 | 0.22 | 560 | 5.28 | 25 | 53 | 73 | 158 | 466 |
| 6 | 25 | 1.0 | 1.17 | 1.68 | 80* | abs. | 20 | 1.1 | 0.22 | 560 | 5.28 | 12.5 | 48 | 93 | 183 | 1075 |
| 7 | 25 | 1.0 | 1.17 | 1.68 | 72* | 8 | 20 | 1.1 | 0.22 | 600 | 2.64 | 25 | 50 | 95 | 194 | 572 |
| 8 | 25 | 1.0 | 1.17 | 1.68 | 43* | 37 | 20 | 1.1 | 0.22 | 600 | 2.64 | 25 | 35 | 93 | 133 | 391 |

Ethylbenzene dehydrogenation - Fluid bed GHSV = (600 ± 2) h −1Nl/h/l cat. bed. LHSV = 0.66 l EB/h/l cat. bed EB: Ethylbenze; *: Nitrogen; **: referring to the active part In the first catalytic test each catalyst was reduced, according to the procedure already described, before carrying out the dehydrogenation reaction.

The ethylbenzene and nitrogen and/or hydrogen or any gaseous inert product were volumetrically dosed to the reactor. A micropump with a syringe was used for the ethylbenzene in liquid phase. For the other gaseous components in co-feed, previously calibrated rotametres were used.

The ethylbenzene before being introduced into the catalytic bed was sent with the inert product used in the co-feed to an evaporator, operating at a temperature of 200° C., placed under the oven in which the reactor was housed and hermetically connected to the latter. The evaporated and inert products were preheated in the specific preheating zone before being introduced into the catalytic bed.

The effluent of the reactor during the reaction and stripping phases was cooled in a trap immersed in liquid nitrogen in which the non-reacted ethylbenzene, styrene and condensable by-products were condensed. The effluent of the trap was sent into an evacuated bag in which hydrogen, the inert product and light $C_1$–$C_3$ hydrocarbons deriving from the cracking reactions, were recovered.

The liquid fraction was weighed and analyzed by gas-chromatography by means of a gaschromatograph hp 5890 equipped with a capillary column CP WAX 10. The dosing

What is claimed is:

1. A process for dehydrogenating ethylbenzene to styrene consisting of:
    a) reacting in a reactor, operating at a temperature of between 450 and 700° C., at a pressure of between 0.1 and 3 atm and with GHSV space velocity of between 100 and 10000 $h^{-1}$ (normal-liters of hydrocarbon/h× liter of catalyst), the ethylbenzene with the catalytic system containing chromium oxide, tin oxide, at least one oxide of an alkaline metal (M) and an alumina carrier, in delta or theta phase or in a mixture of delta+theta or theta+alpha or delta+theta+alpha phases, modified with silica, characterized in that:
    the chromium expressed as $Cr_2O_3$, is in a quantity of between 6 and 30% by weight;
    the tin, expressed as SnO, is in a quantity of between 0.1 and 3.5% by weight;
    the alkaline metal, expressed as $M_2O$, is in a quantity of between 0.4 and 3% by weight;
    the silica is in a quantity of between 0.08 and 3% by weight, the component to 100 being alumina;
    b) regenerating the catalytic system in a regenerator by burning the coke deposited during the reaction phase operating at a temperature of over 400° C.

2. The process according to claim 1 wherein the catalytic system is diluted with an inert product at a weight concentration of the catalytic system of between 5 and 50%.

3. The process according to claim 2 wherein the inert product is alpha-alumina, optionally modified with alkaline metal oxides and/or silica.

4. The process according to claim 1 wherein an inert gas is fed together with the ethylbenzene.

5. The process according to claim 4 wherein the volumetric ratio inert gas/ethylbenzene is between 1 and 6.

6. The process according to claim 5 wherein the volumetric ratio inert gas/ethylbenzene is between 2 and 4.

7. The process according to claim 1 wherein the reactor and the regenerator are of the fluid bed type.

8. The process according to claim 7 wherein the dehydrogenation is carried out at a temperature of between 450 and 650° C., at a pressure which is atmospheric or slightly higher, at a GHSV space velocity of between 100 and 1000 $h^{-1}$ and with a residence time of the catalyst in the fluid bed zone varying from 5 to 30 minutes.

9. The process according to claim 8 wherein the space velocity is between 150 and 200 $h^{-1}$ and the residence time of the catalyst varies from 10 to 15 minutes.

10. The process according to claim 7 wherein the regeneration is carried out with air or oxygen or another combustion-supporting gas at a temperature which is higher than the average temperature of the reactor, at a pressure which is atmospheric or slightly higher, at a space velocity of between 100 and 1000 $h^{-1}$ and with a residence time of the solid varying from 5 to 60 minutes.

11. The process according to claim 1 wherein within the catalyst:

the chromium expressed as $Cr_2O_3$, is in a quantity of between 13 and 25%;

the tin, expressed as SnO, is in a quantity of between 0.2 and 2.8%;

the alkaline metal, expressed as $M_2O$, is in a quantity of between 0.5 and 2.5.

12. The process according to claim 1 or 11 wherein the alkaline metal in the catalyst is potassium.

13. The process according to claim 1 or 11 wherein the carrier has a surface area of less than 150 $m^2/g$.

* * * * *